United States Patent
Chakravarti et al.

(10) Patent No.: US 9,212,113 B2
(45) Date of Patent: Dec. 15, 2015

(54) METHOD AND SYSTEM FOR PRODUCING A SYNTHESIS GAS USING AN OXYGEN TRANSPORT MEMBRANE BASED REFORMING SYSTEM WITH SECONDARY REFORMING AND AUXILIARY HEAT SOURCE

(71) Applicants: Shrikar Chakravarti, East Amherst, NY (US); Raymond F. Drnevich, Clarence Center, NY (US); Ines C. Stuckert, Grand Island, NY (US); Minish M. Shah, East Amherst, NY (US)

(72) Inventors: Shrikar Chakravarti, East Amherst, NY (US); Raymond F. Drnevich, Clarence Center, NY (US); Ines C. Stuckert, Grand Island, NY (US); Minish M. Shah, East Amherst, NY (US)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 0 days.

(21) Appl. No.: 14/261,781

(22) Filed: Apr. 25, 2014

(65) Prior Publication Data

US 2014/0323598 A1 Oct. 30, 2014

Related U.S. Application Data

(60) Provisional application No. 61/816,326, filed on Apr. 26, 2013, provisional application No. 61/874,077, filed on Sep. 5, 2013, provisional application No. 61/910,697, filed on Dec. 2, 2013.

(51) Int. Cl.
*C07C 29/151* (2006.01)
*C07C 29/152* (2006.01)
(Continued)

(52) U.S. Cl.
CPC ............... *C07C 29/1518* (2013.01); *C01B 3/02* (2013.01); *C01B 3/382* (2013.01); *C01B 3/384* (2013.01);
(Continued)

(58) Field of Classification Search
CPC .............. C01B 3/02; C01B 3/36; C01B 3/32; C01B 3/34; C01B 3/38; C01B 3/382; C01B 3/366; C01B 3/386; C01B 3/40
USPC .................................................. 518/702, 703
See application file for complete search history.

(56) References Cited

U.S. PATENT DOCUMENTS

| 4,650,814 A | 3/1987 | Keller |
|---|---|---|
| 5,975,130 A | 11/1999 | Ligh et al. |

(Continued)

FOREIGN PATENT DOCUMENTS

| EP | 0 926 096 A1 | 6/1999 |
|---|---|---|
| EP | 0 984 500 A2 | 3/2000 |

(Continued)

OTHER PUBLICATIONS

Friedemann Marschner et al., "Gas Production", Ullmann's Encyclopedia of Industrial Chemistry, Jun. 15, 2000, pp. 1-21, XP002253967.

(Continued)

*Primary Examiner* — Jafar Parsa
*Assistant Examiner* — Medhanit Bahta
(74) *Attorney, Agent, or Firm* — Ralph J. Mancini

(57) ABSTRACT

A method and system for producing a synthesis gas in an oxygen transport membrane based reforming system is disclosed that carries out a primary reforming process within a reforming reactor, and a secondary reforming process within an oxygen transport membrane reactor and in the presence of heat generated from a oxygen transport membrane reactor and an auxiliary source of heat. The auxiliary source of heat is disposed within the reactor housing proximate the reforming reactors and may include an auxiliary reactively driven oxygen transport membrane reactor or a ceramic burner.

11 Claims, 5 Drawing Sheets

(51) Int. Cl.
*C01B 3/02* (2006.01)
*C01B 3/38* (2006.01)
*C01B 13/02* (2006.01)

(52) U.S. Cl.
CPC ............. *C01B 13/0251* (2013.01); *C01B 3/386* (2013.01); *C01B 2203/0233* (2013.01); *C01B 2203/0283* (2013.01); *C01B 2203/043* (2013.01); *C01B 2203/0822* (2013.01); *C01B 2203/0827* (2013.01); *C01B 2203/142* (2013.01)

(56) References Cited

U.S. PATENT DOCUMENTS

| | | | |
|---|---|---|---|
| 6,048,472 | A | 4/2000 | Nataraj et al. |
| 6,110,979 | A | 8/2000 | Nataraj et al. |
| 6,114,400 | A | 9/2000 | Nataraj et al. |
| 6,214,314 | B1 | 4/2001 | Abbott |
| 6,293,084 | B1 | 9/2001 | Drnevich et al. |
| 6,296,686 | B1 | 10/2001 | Prasad et al. |
| 6,382,958 | B1 | 5/2002 | Bool, III et al. |
| 6,394,043 | B1 | 5/2002 | Bool, III et al. |
| 6,562,104 | B2 | 5/2003 | Bool, III et al. |
| 7,261,751 | B2 | 8/2007 | Dutta et al. |
| 7,470,811 | B2 | 12/2008 | Thiebaut |
| 7,786,180 | B2 | 8/2010 | Fitzpatrick |
| 7,856,829 | B2 | 12/2010 | Shah et al. |
| 8,196,387 | B2 | 6/2012 | Shah et al. |
| 8,262,755 | B2 | 9/2012 | Repasky et al. |
| 8,349,214 | B1 | 1/2013 | Kelly et al. |
| 8,419,827 | B2 | 4/2013 | Repasky et al. |
| 2003/0039608 | A1 | 2/2003 | Shah et al. |
| 2004/0221722 | A1 | 11/2004 | Prasad et al. |
| 2007/0041894 | A1 | 2/2007 | Drnevich |
| 2007/0289215 | A1 | 12/2007 | Hemmings et al. |
| 2007/0292342 | A1 | 12/2007 | Hemmings et al. |
| 2008/0141672 | A1 | 6/2008 | Shah et al. |
| 2008/0302013 | A1 | 12/2008 | Repasky et al. |
| 2009/0120379 | A1 | 5/2009 | Bozzuto et al. |
| 2011/0076213 | A1 | 3/2011 | Carolan et al. |
| 2011/0142722 | A1 | 6/2011 | Hemmings et al. |
| 2011/0240924 | A1* | 10/2011 | Repasky ...................... 252/373 |
| 2013/0009100 | A1* | 1/2013 | Kelly et al. .................. 252/373 |
| 2013/0009102 | A1 | 1/2013 | Kelly et al. |
| 2014/0183866 | A1 | 7/2014 | Kromer et al. |
| 2014/0319424 | A1 | 10/2014 | Chakravarti et al. |
| 2014/0319427 | A1 | 10/2014 | Chakravarti et al. |
| 2014/0323598 | A1 | 10/2014 | Chakravarti et al. |

FOREIGN PATENT DOCUMENTS

| | | |
|---|---|---|
| EP | 0 989 093 A2 | 3/2000 |
| EP | 1 504 811 A1 | 2/2005 |
| WO | WO 2013/062413 A1 | 5/2013 |
| WO | WO 2014/107707 A2 | 7/2014 |
| WO | WO 2014/176022 A1 | 10/2014 |

OTHER PUBLICATIONS

Lee Rosen, Nick Degenstein; Minish Shah; Jamie Wilson; Sean Kelly; John Peck; and Max Christie; "Development of Oxygen Transport Membranes for Coal-Based Power Generation"; ScienceDirect (Available online at www.sciencedirect.com); Energy Procedia 4 (2011) pp. 750-755.

* cited by examiner

METHOD AND SYSTEM FOR PRODUCING A SYNTHESIS GAS USING AN OXYGEN TRANSPORT MEMBRANE BASED REFORMING SYSTEM WITH SECONDARY REFORMING AND AUXILIARY HEAT SOURCE

CROSS REFERENCE TO RELATED APPLICATIONS

This application claims priority to and the benefit of U.S. provisional patent application Ser. Nos. 61/816,326 filed on Apr. 26, 2013; 61/874,077 filed on Sep. 5, 2013; and 61/910,697 filed on Dec. 2, 2013, the disclosures of which are incorporated by reference herein.

FIELD OF THE INVENTION

The present invention relates to a method and system for producing a synthesis gas in an oxygen transport membrane based reforming system, and more particularly, a method and system for producing a synthesis gas in an oxygen transport membrane based reforming system that provides both primary and secondary reforming and an auxiliary heat source.

BACKGROUND

Synthesis gas containing hydrogen and carbon monoxide is used for a variety of industrial applications, for example, the production of hydrogen, chemicals and synthetic fuel production. Conventionally, the synthesis gas is produced in a fired reformer in which natural gas and steam is reformed in nickel catalyst containing reformer tubes at high temperatures (e.g., 850° C. to 1000° C.) and moderate pressures (e.g., 16 to 30 bar) to produce the synthesis gas. The endothermic heating requirements for steam methane reforming reactions occurring within the reformer tubes are provided by burners firing into the furnace that are fueled by part of the natural gas. In order to increase the hydrogen content of the synthesis gas produced by the steam methane reforming (SMR) process, the synthesis gas can be subjected to water-gas shift reactions to react residual steam in the synthesis gas with the carbon monoxide.

A well established alternative to steam methane reforming is the non-catalytic partial oxidation process (POx) whereby a sub-stoichiometric amount of oxygen is allowed to react with the natural gas feed creating steam and carbon dioxide at high temperatures. The high temperature residual methane is reformed through reactions with the high temperature steam and carbon dioxide.

An attractive alternative process for producing synthesis gas is the autothermal reforming (ATR) process which uses oxidation to produce heat with a catalyst to permit reforming to occur at lower temperatures than the POx process. Similar to the POx process, oxygen is required to partially oxidize natural gas in a burner to provide heat, high temperature carbon dioxide and steam to reform the residual methane. Some steam needs to be added to the natural gas to control carbon formation on the catalyst. However, both the ATR and POx processes require separate air separation units (ASU) to produce high-pressure oxygen, which adds complexity as well as capital and operating cost to the overall process.

When the feedstock contains significant amounts of heavy hydrocarbons, SMR and ATR processes, are typically preceded by a pre-reforming step. Pre-reforming is a catalyst based process for converting higher hydrocarbons to methane, hydrogen, carbon monoxide and carbon dioxide. The reactions involved in pre-reforming are generally endothermic. Most pre-reformers on natural gas steams operate in the endothermic area and operate adiabatically, and thus the pre-reformed feedstock leaves at a lower temperature than the feedstock entering the pre-reformer. Another process that will be discussed in this invention is the secondary reforming process, which is essentially an autothermal process that is fed the product from a steam methane reforming process. Thus, the feed to a secondary reforming process is primarily synthesis gas from steam methane reforming. Depending on the end application, sonic natural gas may bypass the SMR process and be directly introduced into the secondary reforming step. Also, when a SMR process is followed by a secondary reforming process, the SMR may operate at a lower temperature, e.g. 650° C. to 825° C. versus 850° C. to 1000° C.

As can be appreciated, the conventional methods of producing a synthesis gas such as have been discussed above are expensive and require complex installations. To overcome the complexity and expense of such installations it has been proposed to generate the synthesis gas within reactors that utilize an oxygen transport membrane to supply oxygen and thereby generate the heat necessary to support endothermic heating requirements of the steam methane reforming reactions. A typical oxygen transport membrane has a dense layer that, while being impervious to air or other oxygen containing gas, will transport oxygen ions when subjected to an elevated operational temperature and a difference in oxygen partial pressure across the membrane.

Examples of oxygen transport membrane based reforming systems used in the production of synthesis gas can be found in U.S. Pat. Nos. 6,048,472; 6,110,979; 6,114,400; 6,296,686; 7,261,751; 8,262,755; and 8,419,827. There is an operational problem with all of these oxygen transport membrane based systems because such oxygen transport membranes need to operate at high temperatures of around 900° C. to 1100° C. Where hydrocarbons such as methane and higher order hydrocarbons are subjected to such high temperatures within the oxygen transport membrane, excessive carbon formation occurs, especially at high pressures and low steam to carbon ratios. The carbon formation problems are particularly severe in the above-identified prior art oxygen transport membrane based systems. A different approach to using an oxygen transport membrane based reforming system in the production of synthesis gas is disclosed in U.S. Pat. No. 8,349,214 which provides a oxygen transport membrane based reforming system that uses hydrogen and carbon monoxide as part of the reactant gas feed to the oxygen transport membrane tubes and minimizes the hydrocarbon content of the feed entering the permeate side of the oxygen transport membrane tubes. Excess heat generated within the oxygen transport membrane tubes is transported mainly by radiation to the reforming tubes made of conventional materials. Use of low hydrocarbon content high hydrogen and carbon monoxide feed to the oxygen transport membrane tubes addresses many of the highlighted problems with the earlier oxygen transport membrane systems.

Other problems that arise with the prior art oxygen transport membrane based reforming systems are the cost of the oxygen transport membrane modules and the lower than desired durability, reliability and operating availability of such oxygen transport membrane based reforming systems. These problems are the primary reasons that oxygen transport membranes based reforming systems have not been successfully commercialized. Advances in oxygen transport membrane materials have addressed problems associated with oxygen flux, membrane degradation and creep life, but there is much work left to be done to achieve commercially viable oxygen transport membrane based reforming systems from a cost standpoint as well as from an operating reliability and availability standpoint.

The present invention addresses the aforementioned problems by providing an improved process for making synthesis gas using a reactively-driven oxygen transport membrane based system, which consists of two reactors that can be in the form of sets of catalyst containing tubes—reforming reactor and oxygen transport membrane reactor. Partial oxidation and some reforming occurs at the permeate (i.e. catalyst containing) side of the oxygen transport membranes and a reforming process facilitated by a reforming catalyst occurs in the reforming reactor in close proximity to the oxygen transport membrane reactor. The partial oxidation process, which is exothermic, and the reforming process, which is endothermic, both occur within the oxygen transport membrane based reforming system and thus have a high degree of thermal integration so that heat released in the oxidation process supplies the heat absorbed by the reforming process. Specifically, improvements to the reactively-driven oxygen transport membrane based system include modifications to the reactively-driven oxygen transport membrane based system to carry out both a primary reforming process in a catalyst filled reforming reactor as well as a secondary reforming process within the catalyst containing oxygen transport membrane reactor and to provide a source of auxiliary heat to balance the reforming duty between the oxygen transport membrane reactor and the auxiliary heat source.

SUMMARY OF THE INVENTION

The present invention may be characterized as a method for producing a synthesis gas in an oxygen transport membrane based reforming system, which may comprise at least two reactors that can be in the form of sets of catalyst containing tubes, including a reforming reactor and an oxygen transport membrane reactor, the method comprising the steps of: (i) reforming a hydrocarbon containing feed stream in a reforming reactor in the presence of a reforming catalyst disposed in the reforming reactor and heat to produce a reformed synthesis gas stream; (ii) feeding the reformed synthesis gas stream to a reactant side of a reactively driven and catalyst containing oxygen transport membrane reactor, wherein the oxygen transport membrane reactor includes at least one oxygen transport membrane element configured to separate oxygen from an oxygen containing stream at the oxidant side of the reactively driven and catalyst containing oxygen transport membrane reactor and transport the separated oxygen to the reactant side through oxygen ion transport when subjected to an elevated operational temperature and a difference in oxygen partial pressure across the at least one oxygen transport membrane element; (iii) reacting a portion of the reformed synthesis gas stream with oxygen permeated through the at least one oxygen transport membrane element to produce the difference in oxygen partial pressure across the at least one oxygen transport membrane element and generate reaction products and heat; and (iv) reforming unreformed hydrocarbon gas in the reformed synthesis gas stream in the presence of catalysts contained in the oxygen transport membrane reactor, the reaction products and the heat to produce a synthesis gas product stream. A first portion of the heat required for the initial or primary reforming step is provided by the reactively driven and catalyst containing oxygen transport membrane reactor and a second portion of the heat required for the primary reforming step is transferred from an auxiliary heat source disposed proximate the reforming reactor.

The invention may also be characterized as an oxygen transport membrane based reforming system comprising: (a) a reactor housing; (b) a reforming reactor disposed in the reactor housing and configured to reform a hydrocarbon containing feed stream in the presence of a reforming catalyst disposed in the reforming reactor and heat to produce a reformed synthesis gas stream; (c) a reactively driven oxygen transport membrane reactor disposed in the reactor housing proximate the reforming reactor and configured to receive the reformed synthesis gas stream and react a portion of the reformed synthesis gas stream with permeated oxygen and generate reaction products and heat, including a first portion of the heat required by the reforming reactor; and (d) an auxiliary heat source disposed in the reactor housing proximate the reforming reactor and configured to supply a second portion of the heat required by the reforming reactor to produce the reformed synthesis gas stream.

The reactively driven oxygen transport membrane reactor is further configured to reform any unreformed hydrocarbon gas in the reformed synthesis gas stream in the presence of one or more catalysts and some of the heat generated by the reaction of the reformed synthesis gas stream and permeated oxygen to produce a synthesis gas product stream. At a temperature of about 730° C. at the exit of the reforming reactor and a temperature of about 995° C. at the exit of the OTM reactor, the module of the synthesis gas product stream is between about 1.85 and 2.15 or more and is dependent on the amount of heat supplied to the reforming reactor from the auxiliary heat source. More specifically, at the specified temperatures, the module of the synthesis gas product stream rises from a minimum of about 1.85 when the percentage of heat supplied to the reforming reactor from the auxiliary heat source is less than 15% to a maximum of about 2.15 when the percentage of heat supplied to the reforming reactor from the auxiliary heat source is greater than about 85%. Put another way, at temperatures of about 730° C. and 995° C. at the exit of the reforming reactor and OTM reactor respectively, the module of the synthesis gas product stream will be between about 1.85 and 2.00 when the second portion of heat supplied to the reforming reactor from the auxiliary heat source is 50% or less of the total required heat to be supplied to the reforming reactor and between about 2.00 and 2.15 when the second portion of heat supplied to the reforming reactor from the auxiliary heat source is more than 50% of the total required heat to be supplied to the reforming reactor. As indicated above, the actual module of the synthesis gas product stream is also dependent on the reforming temperatures within the oxygen transport membrane based reforming system, and in particular, the temperature at the exit of the reforming reactor. For example, if the temperature at the exit of the reforming reactor is raised to a temperature of between 800° C. and 900° C., the range of module for the synthesis gas product stream would be expected to increase to perhaps between about 1.90 to 2.25 or more depending on the amount of heat supplied to the reforming reactor from the auxiliary heat source.

In addition to the variation of the module of the synthesis gas product stream based on the reforming duty split between the first portion of heat and the second portion of heat designed into the oxygen transport membrane based reforming system, the hydrogen to carbon monoxide ratio ($H_2/CO$) of the synthesis gas product stream is also varied slightly between about 2.95 and 3.10 at a reforming reactor exit temperature of about 730° C. and depending on the amount of heat supplied to the reforming reactor from the auxiliary heat source. The carbon monoxide to carbon dioxide ratio (CO/CO2) of the synthesis gas product stream also varies between about 2.50 and 3.30 at an exit temperature of about 730° C.

and depending on the reforming duty split between the first portion of heat and the second portion of heat.

The auxiliary heat source may be designed to provide between about 15% and 85% of the heat required for the reforming of the hydrocarbon containing feed stream. The auxiliary heat source may be in the form of one or more auxiliary oxygen transport membrane reactors or one or more ceramic burners disposed within the reactor housing and in close proximity to the reforming reactor.

BRIEF DESCRIPTION OF THE DRAWINGS

While the specification concludes with claims distinctly pointing out the subject matter that applicants regard as their invention, it is believed that the invention will be better understood when taken in connection with the accompanying drawings in which:

DETAILED DESCRIPTION

Figure 1:
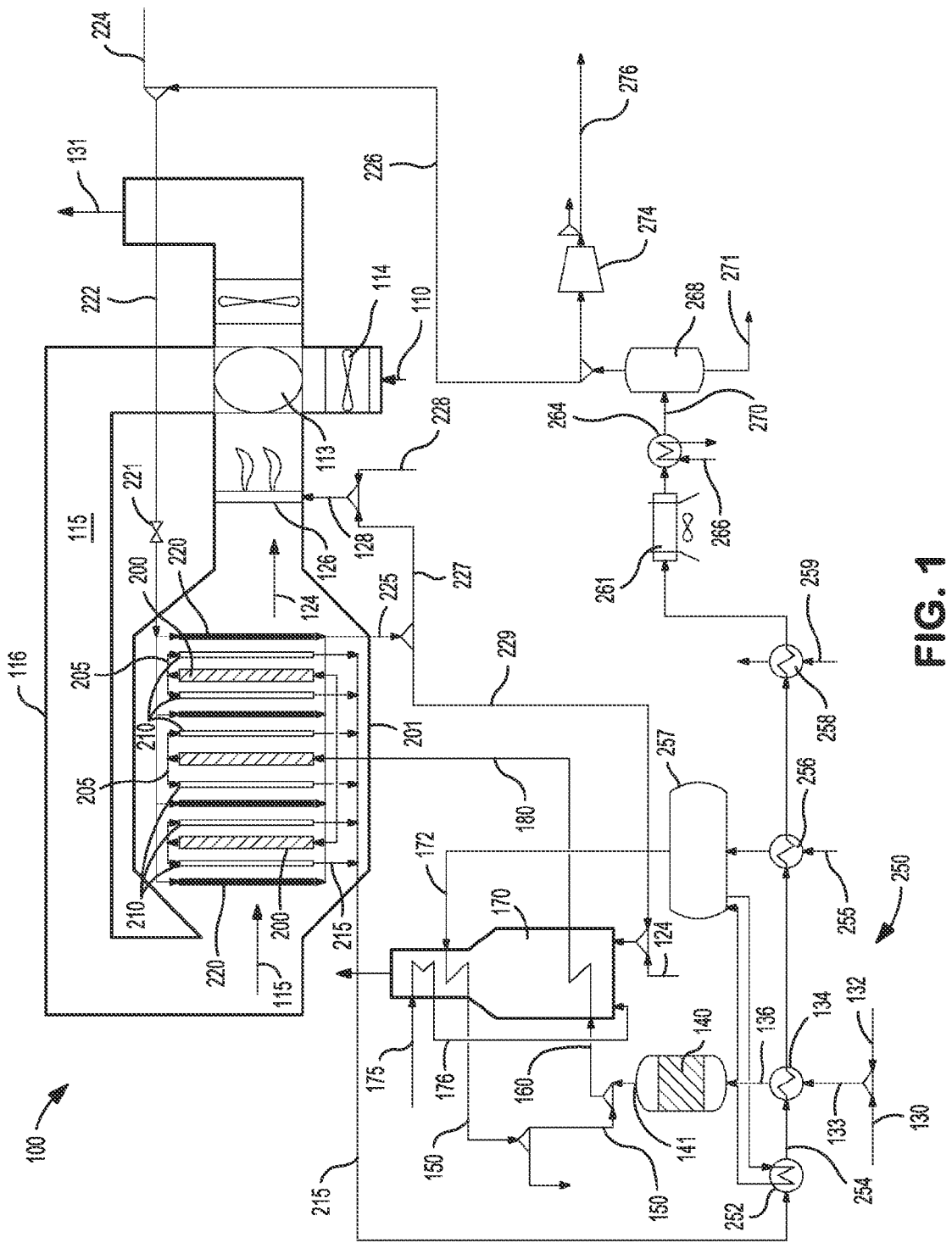
FIG. 1 is a schematic illustration of an embodiment of an oxygen transport membrane based reforming system designed to carry out both a primary reforming process and a secondary reforming process within the oxygen transport membrane reactor using an auxiliary heat source comprising a second oxygen transport membrane reactor.

FIG. 1 provides a schematic illustration of an embodiment of an oxygen transport membrane based reforming system 100 in accordance with the present invention. As seen therein, an oxygen containing stream 110, such as air, is introduced to the system by means of a forced draft (FD) fan 114 into a heat exchanger 113 for purposes of preheating the oxygen containing feed stream 110. Heat exchanger 113 is preferably a high efficiency, cyclic and continuously rotating ceramic regenerator disposed in operative association with the oxygen containing feed stream 110 and a heated oxygen depleted retentate stream 124. The incoming air feed stream 110 is heated in the ceramic regenerator 113 to a temperature in the range of about 850° C. to 1050° C. to produce a heated air feed stream 115.

The oxygen depleted air leaves the oxygen transport membrane reforming tubes as heated oxygen depleted retentate stream 124 at the same or slightly higher temperature than the heated air feed stream 115. Any temperature increase, typically less than about 30° C., is attributable to the portion of energy generated by oxidizing reaction of hydrogen and carbon monoxide in the oxygen transport membrane tubes and transferred by convection to the oxygen depleted retentate stream 124.

The temperature of this oxygen depleted retentate stream 124 is heated back to a temperature between about 1050° C. and 1200° C. prior to being directed to the heat exchanger or ceramic regenerator 113. This increase in temperature of the oxygen depleted retentate stream 124 is preferably accomplished by use of a duct burner 126, which facilitates combustion of a supplemental fuel stream 128 using some of the residual oxygen in the retentate stream 124 as the oxidant. Though not shown, an alternative means is to combust the supplemental fuel stream 128 with a separate air stream in duct burner 126 and then mix the hot flue gas with the oxygen depleted retentate stream 124. In the ceramic heat exchanger or regenerator 113, the heated, oxygen depleted retentate stream 124 provides the energy to raise the temperature of the incoming feed air stream 110 from ambient temperature to a temperature between about 850° C. to 1050° C. The resulting cold retentate stream exiting the ceramic heat exchanger, typically containing less than about 5% oxygen, leaves the oxygen transport membrane based reforming system 100 system as exhaust gas 131 at a temperature of around 150° C.

Although not shown in FIG. 1, an alternate embodiment of the oxygen transport membrane based reforming system 100 could dispose the duct burner and supplemental fuel stream upstream of the reactors in intake duct 116. Such arrangement would allow use of a smaller ceramic regenerator 113 and less severe operating conditions for the ceramic regenerator 113.

The hydrocarbon containing feed stream 130, preferably natural gas, to be reformed is typically mixed with a small amount of hydrogen or hydrogen-rich gas 132 to form a combined hydrocarbon feed 133 and then preheated to around 370° C. in heat exchanger 134 that serves as a feed pre-heater, as described in more detail below. Since natural gas typically contains unacceptably high level of sulfur species, a small amount of hydrogen or hydrogen-rich gas 132 is added to facilitate desulfurization. Preferably, the heated feed stream 136 undergoes a sulfur removal process via device 140 such as hydro-treating to reduce the sulfur species to $H_2S$, which is subsequently removed in a guard bed using material like ZnO and/or CuO. The hydro-treating step also saturates any alkenes present in the hydrocarbon containing feed stream. Further, since natural gas generally contains higher hydrocarbons that will break down at high temperatures to form unwanted carbon deposits that adversely impact the reforming process, the natural gas feed stream is preferably pre-reformed in an adiabatic pre-reformer, which converts higher hydrocarbons to methane, hydrogen, carbon monoxide, and carbon dioxide. Also contemplated but not shown is an embodiment where the pre-reformer is a heated pre-reformer that may be thermally coupled with oxygen transport membrane based reforming system.

Superheated steam 150 is added to the pre-treated natural gas and hydrogen feed stream 141, as required, to produce a mixed feed stream 160 with a steam to carbon ratio between about 1.0 and 2.5, and more preferably between about 1.2 and 2.2. The superheated steam 150 is preferably between about 15 bar and 80 bar and between about 300° C. and 600° C. and generated in a fired heater 170 using a source of process steam 172. As seen in FIG. 1, the fired heater 170 is configured to combust a supplemental fuel stream 174 and optionally a portion of the off-gas 229 produced by the oxygen transport membrane based reforming system using air 175 as the oxidant to heat the process steam 172 to superheated steam 150.

In the illustrated embodiment, a source of air 175 is heated in the fired heater 170 to produce a heated air stream 176 to be used as the oxidant in the fired heated 170. The mixed feed stream 160 is also heated in the fired heater 170 producing a heated mixed feed stream 180. The heated mixed feed stream 180 has a temperature preferably between about 450° C. and 650° C. and more preferably a temperature between about 500° C. and 600° C.

The illustrated embodiment of the oxygen transport membrane based reforming system 100 comprises three reactors (200, 210, 220) disposed in a single reactor housing 201. The first reactor is a reforming reactor 200 which comprises reforming catalyst containing tubes configured to reform the heated mixed feed stream 180 containing a hydrocarbon feed and steam in the presence of a conventional reforming catalyst disposed in the reforming tubes and heat to produce a reformed synthesis gas stream 205. The temperature of the reformed hydrogen-rich synthesis gas stream is typically designed to be between 650° C. and 850° C.

The reformed synthesis gas stream 205 is then fed as an influent to the second reactor which is an oxygen transport membrane reactor 210. More particularly, reformed synthesis gas stream 205 is fed to a reactant side of a reactively driven and catalyst containing oxygen transport membrane reactor 210. The reactively driven, oxygen transport membrane reactor 210 includes one or more oxygen transport membrane elements or tubes each having an oxidant side and a reactant side that are disposed proximate to the reforming tubes. Each of the oxygen transport membrane elements or tubes are configured to separate oxygen from the heated oxygen containing stream 115 contacting the oxidant side to the reactant side through oxygen ion transport. The oxygen ion transport occurs when the oxygen transport membrane elements or tubes are subjected to elevated operational temperatures and there is a difference in oxygen partial pressure across the oxygen transport membrane elements or tubes.

A portion of the reformed synthesis gas stream 205 fed to the reactant side of the oxygen transport membrane reactor 210 immediately reacts with oxygen permeated through the oxygen transport membrane elements or tubes to produce the difference in oxygen partial pressure across the oxygen transport membrane elements or tubes which drives the oxygen ion transport and separation. This reaction produces reaction products and heat. A portion of the heat produced by the reaction the reformed synthesis gas stream 205 and the permeated oxygen is transferred via convection to the oxygen depleted retentate stream and another portion of the heat is transferred via radiation to the reforming reactor 200.

The oxygen transport membrane reactor 210 is further configured to reform unreformed hydrocarbon gas in the reformed synthesis gas stream 205 and produce a synthesis gas product stream 215. This secondary reforming occurs in the presence of one or more reforming catalysts contained in the oxygen transport membrane elements or tubes, reaction products (e.g. from the reaction of a portion of the reformed synthesis gas stream 205 and oxygen permeate) and the third portion of the energy or heat produced by the same reaction. The synthesis gas product stream 215 leaving the oxygen transport membrane reactor 210 is preferably at a temperature between about 900° C. and 1050° C.

The third reactor in the illustrated embodiment is an auxiliary oxygen transport membrane reactor 220 that is configured to provide an auxiliary source of radiant heat to the reforming reactor 200. This auxiliary reactor 220 or heat source preferably provides between about 15% and 85% of the heat required for the initial reforming of the heated mixed feed stream 180 that occurs in the reforming reactor 200. The auxiliary oxygen transport membrane reactor 220 is also a reactively driven oxygen transport membrane reactor 220 that comprises a plurality of oxygen transport membrane elements or tubes disposed proximate to or in a juxtaposed orientation with respect to the reforming reactor 200. The auxiliary oxygen transport membrane reactor 220 is configured to also separate or permeate oxygen from the oxygen containing stream 115 contacting the oxidant side of the oxygen transport membrane elements or tubes to the reactant side of the oxygen transport membrane elements or tubes through oxygen ion transport. The permeated oxygen reacts with a low pressure hydrogen containing stream 222, preferably less than about 3 bar, that is fed via a valve 221 to the reactant side of the oxygen transport membrane elements or tubes to produce the difference in oxygen partial pressure across the oxygen transport membrane element and to produce an auxiliary reaction product stream 225 and heat.

In the illustrated embodiment, the low pressure hydrogen containing stream 222 is a hydrogen and light hydrocarbon containing stream that preferably includes a recirculated portion 226 of the synthesis gas product stream and optionally a supplementary fuel 224. A portion of the reaction product stream 225 exiting the reactant side of the oxygen transport membrane elements or tubes of the oxygen transport membrane reactor 220 is an off-gas 227 that may be mixed with a supplementary natural gas fuel 228 to the duct burner 126. Another portion of the reaction product stream 225 exiting the reactant side of the oxygen transport membrane elements or tubes is an off-gas 229 that may be mixed with a supplementary natural gas fuel 174 to fired heater 170.

Preferably, the reforming reactor 200 and the oxygen transport membrane reactor 210 are arranged as sets of closely packed tubes in close proximity to one another. The reforming reactor 200 generally consists of reforming tubes. Oxygen transport membrane reactor 210 as well as the auxiliary oxygen transport membrane reactor 220 comprise a plurality of ceramic oxygen transport membrane tubes. The oxygen transport membrane tubes are preferably configured as multilayered ceramic tubes capable of conducting oxygen ions at an elevated operational temperature, wherein the oxidant side of the oxygen transport membrane tubes is the exterior surface of the ceramic tubes exposed to the heated oxygen containing stream and the reactant side or permeate side is the interior surface of the ceramic tubes. Within each of the oxygen transport membrane tubes are one or more catalysts that facilitate partial oxidation and/or reforming, as applicable. Although only three of the reforming tubes are illustrated in FIG. 1 in close proximity to six of the secondary reforming oxygen transport membrane elements or tubes and four of the auxiliary oxygen transport membrane elements or tubes, there could be many of such oxygen transport membrane tubes and many reforming tubes in each oxygen transport membrane based reforming sub-system or assembly as would occur to those skilled in the art. Likewise, there could be multiple oxygen transport membrane based reforming sub-systems or assemblies used in industrial applications of the oxygen transport membrane based reforming system 100.

The oxygen transport membrane elements or tubes used in the embodiments disclosed herein preferably comprise a composite structure that incorporates a dense layer, a porous support and an intermediate porous layer located between the dense layer and the porous support. Each of the dense layer and the intermediate porous layer are capable of conducting oxygen ions and electrons at elevated operational temperatures to separate the oxygen from the incoming air stream. The porous support layer would thus form the reactant side or permeate side. The dense layer and the intermediate porous layer preferably comprise a mixture of an ionic conductive material and an electrically conductive material to conduct oxygen ions and electrons, respectively. The intermediate porous layer preferably has a lower permeability and a smaller average pore size than the porous support layer to distribute the oxygen separated by the dense layer towards the porous support layer. The preferred oxygen transport membrane tubes also include a mixed phase oxygen ion conducting dense ceramic separation layer comprising a mixture of a zirconia based oxygen ion conducting phase and a predominantly electronic conducting perovskite phase. This thin, dense separation layer is implemented on the thicker inert, porous support.

Oxidation catalyst particles or a solution containing precursors of the oxidation catalyst particles are optionally located in the intermediate porous layer and/or in the thicker inert, porous support adjacent to the intermediate porous layer. The oxidation catalyst particles contain an oxidation catalyst, such as gadolinium doped ceria, are selected to promote oxidation of the partially reformed synthesis gas stream in the presence of the permeated oxygen when introduced into the pores of the porous support, on a side thereof opposite to the intermediate porous layer.

The endothermic heating requirements of the reforming process occurring in the reforming reactor 200 is supplied through radiation of some of the heat from the oxygen transport membrane reactor 210 and auxiliary oxygen transport membrane reactor 220 together with the convective heat transfer provided by heated oxygen depleted retentate stream. Sufficient thermal coupling or heat transfer between the heat-releasing ceramic oxygen transport membrane tubes and the heat-absorbing catalyst containing reformer tubes must be enabled within the design of the present reforming system. A portion of the heat transfer between the ceramic oxygen transport membrane tubes and the adjacent or juxtaposed reforming catalyst containing reformer tubes is through the radiation mode of heat transfer whereby surface area, surface view factor, surface emissivity, and non-linear temperature difference between the tubes (e.g., $T_{otm}^4 - T_{reformer}^4$), are critical elements to achieve the desired thermal coupling. Surface emissivity and temperatures are generally dictated by tube material and reaction requirements. The surface area and surface view factor are generally dictated by tube arrangement or configuration within each module and the entire reactor. While there are numerous tube arrangements or configurations that could meet the thermal coupling requirements between the oxygen transport membrane tubes and the reformer tubes, a key challenge is to achieve a relatively high production rate per unit volume which, in turn, depends on the amount of active oxygen transport membrane area contained within the unit volume. An additional challenge to achieving the optimum thermal coupling performance is to optimize the size of the ceramic oxygen transport membrane tubes and the catalyst containing reformer tubes, and more particular the effective surface area ratio, $A_{reformer}/A_{otm}$, of the respective tubes. Of course, such performance optimization must be balanced against the manufacturability requirements, costs, as well as the reliability, maintainability, operating availability of the modules and reactor.

Figure 4:
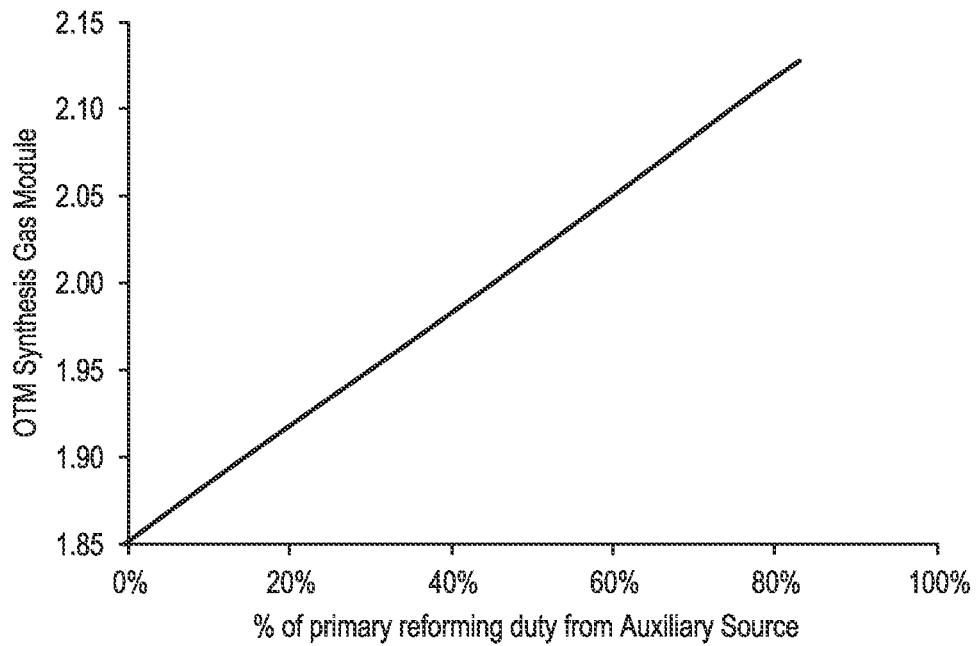
FIG. 4 is a graph that depicts the module of the synthesis gas produced in the oxygen transport membrane based reforming system as a function of the percent of primary reforming duty attributable to the auxiliary heat source.
Figure 5:
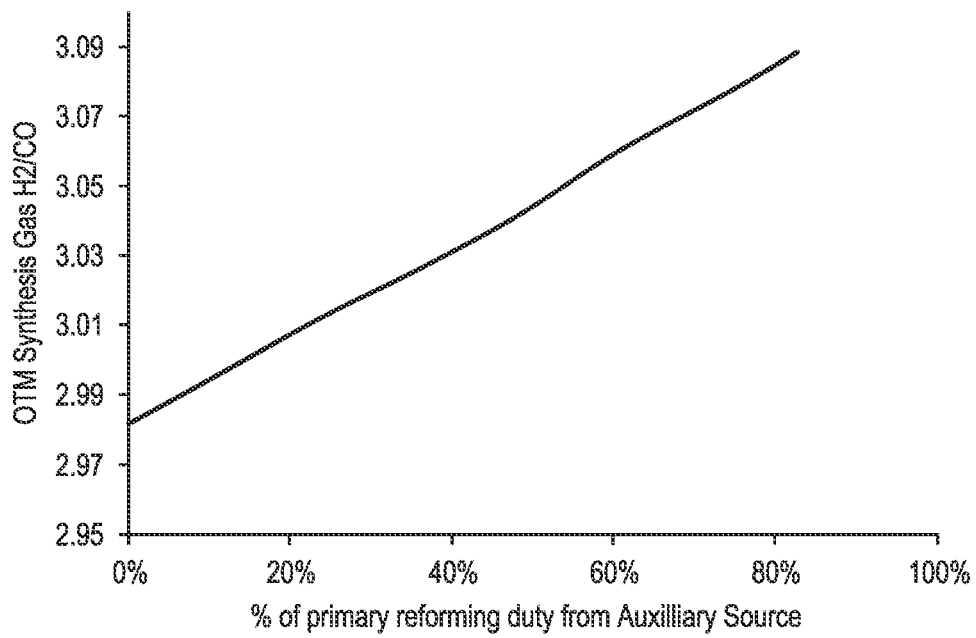
FIG. 5 is a graph that depicts the hydrogen to carbon monoxide ratio ($H_2/CO$) of the synthesis gas produced in the oxygen transport membrane based reforming system as a function of the percent of primary reforming duty attributable to the auxiliary heat source.
Figure 6:
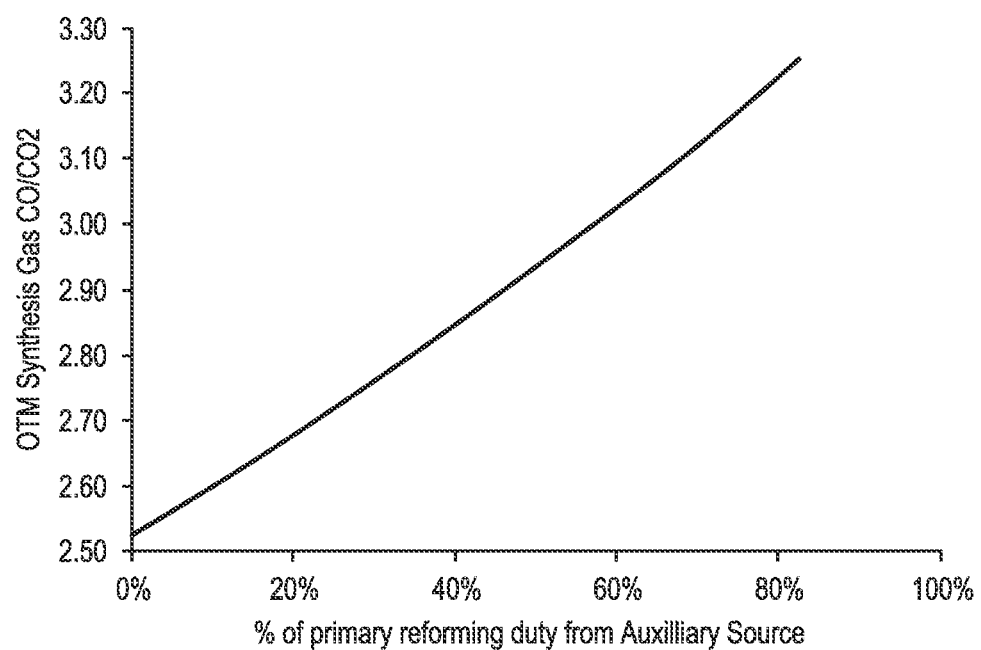
FIG. 6 is a graph that depicts the carbon monoxide to carbon dioxide ratio (CO/CO2) of the synthesis gas produced in the oxygen transport membrane based reforming system as a function of the percent of primary reforming duty attributable to the auxiliary heat source.

Advantageously, it has been found that the module of the synthesis gas product stream produced from the disclosed embodiments of the oxygen transport membrane based reforming system varies depending on the exit stream temperatures and the amount of heat supplied to the reforming reactor from the auxiliary heat source. For example, as depicted in FIG. 4, the module of the synthesis gas product stream produced from the disclosed embodiments, when the temperature at the exit of the reforming reactor is about 730° C. and the temperature at the exit of the OTM reactor is about 995° C., is between about 1.85 and 2.15 or more and is a function of the amount of heat supplied to the reforming reactor from the auxiliary heat source presented as a percentage of total primary reforming duty that comes from the auxiliary heat source. Similarly, as seen in FIG. 5, at a reforming reactor exit temperature of about 730° C. the hydrogen to carbon monoxide ratio ($H_2/CO$) of the synthesis gas product stream is maintained with a small band generally between about 2.95 and 3.10 depending on the amount of heat supplied to the reforming reactor from the auxiliary heat source. Again, the amount of heat supplied to the reforming reactor from the auxiliary heat source is depicted in FIG. 5 as a percentage of total primary reforming duty that comes from the auxiliary heat source. Lastly, as seen in FIG. 6 and at a reforming reactor exit temperature of about 730° C., the carbon monoxide to carbon dioxide ratio (CO/CO2) of the synthesis gas product stream ranges between about 2.50 and 3.30 depending on the amount of heat supplied to the reforming reactor from the auxiliary heat source.

The actual module, $H_2/CO$ ratio and CO/CO2 ratio of the synthesis gas product stream is very much dependent on the exit temperatures realized within the oxygen transport membrane based reforming system. The graphs of FIGS. 4-6 represent a temperature of about 730° C. at the exit of the reforming reactor. If this temperature is raised to a temperature of between about 800° C. and 900° C., the range of module for the synthesis gas product stream would be expected to also increase, perhaps to between about 1.90 to 2.25 or more depending on the amount or percentage of reforming duty heat supplied to the reforming reactor from the auxiliary heat source. Increasing the temperature at the exit of the OTM reactor typically results in a decrease in the module of the synthesis gas.

Figure 2:
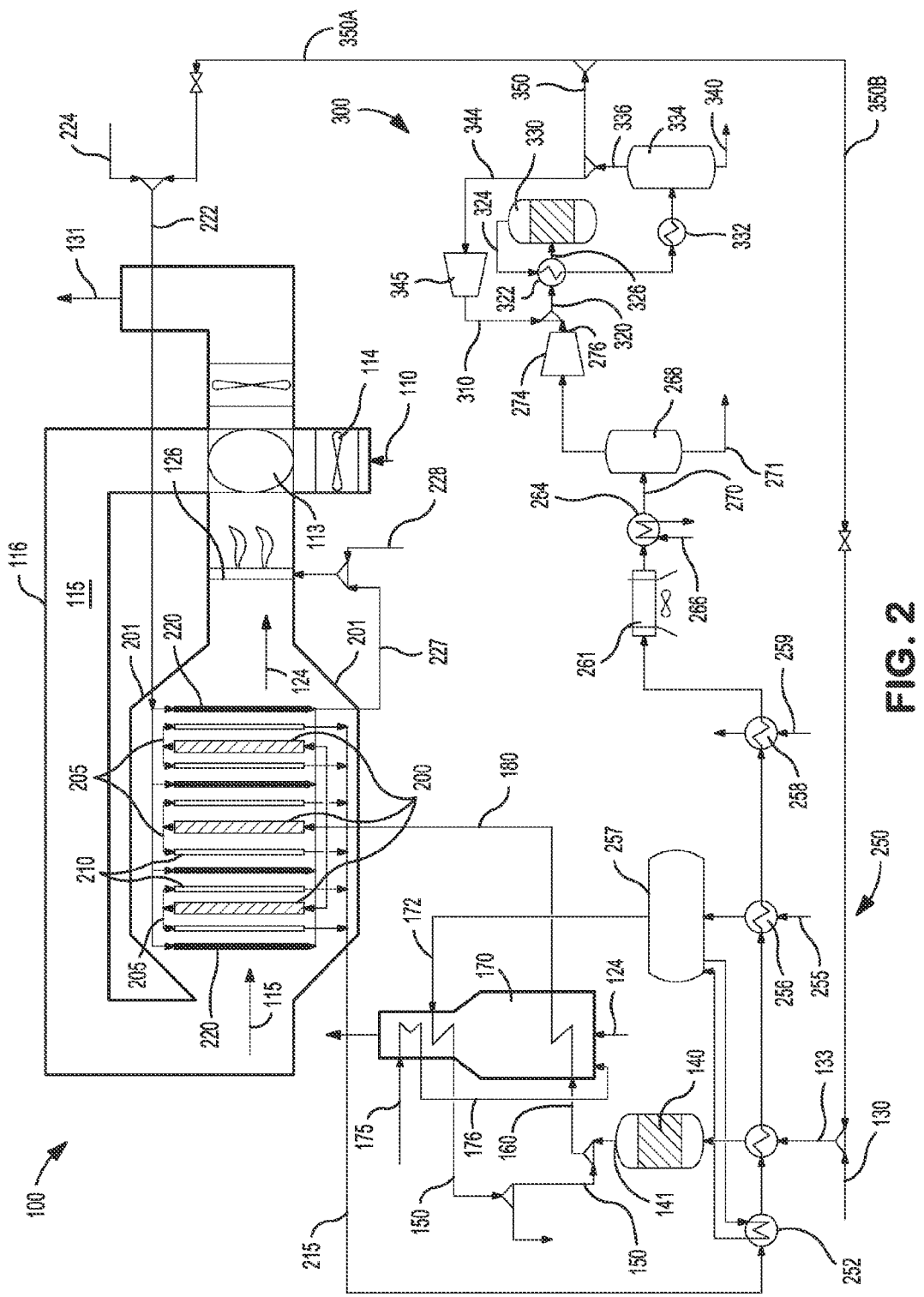
FIG. 2 is a schematic illustration of the oxygen transport membrane based reforming system of FIG. 1 tailored for and integrated with a methanol production process.

As indicated above, the auxiliary heat source is configured, or more preferably designed, to provide between about 15% and 85% of the total heat required for the primary reforming of the hydrocarbon containing feed stream in the reforming reactor. The auxiliary heat source may be an auxiliary oxygen transport membrane reactor as shown in FIGS. 1 and 2 or may comprise one or more ceramic burners as shown, for example, in FIG. 3 described in more detail below. At the low end of the 15% to 85% range, the module of the synthesis gas product stream is around 1.90 whereas at the higher end of the range, the module of the synthesis gas product stream is between about 2.10 and 2.15 or more. An alternative way to characterize the graph of FIG. 4 and the synthesis gas product produced by the presently disclosed oxygen transport membrane based reforming systems is that the module of the synthesis gas product stream is between about 1.85 and 2.00 when the heat supplied from the auxiliary heat source to the reforming reactor is 50% or less of the total required heat to be supplied to the reforming reactor, and between about 2.00 and 2.15 or more when the heat supplied to the reforming reactor from the auxiliary heat source is more than 50% of the total required heat to the reforming reactor. As indicated above, if the temperature at the exit of the reforming reactor is raised, one would expect a corresponding increase in module of the synthesis gas product to 2.25 or more depending on the amount of heat supplied to the reforming reactor from the auxiliary heat source.

As a result, it is possible to design and/or tailor the present oxygen transport membrane based reforming system to produce a synthesis gas having desired characteristics by simply adjusting or modifying the heat duty split between oxygen transport membrane reactor and the auxiliary heat source as well as the exit temperatures. The desired or targeted synthesis gas characteristics will depend of course on the application of the synthesis gas and other system variables, such as stream exit temperatures, methane slip, reactor pressures, etc.

Turning again to FIG. 1, the synthesis gas stream 215 produced by the oxygen transport membrane reactor 210 generally contains hydrogen, carbon monoxide, unconverted methane, steam, carbon dioxide and other constituents. A significant portion of the sensible heat from the synthesis gas stream 215 can be recovered using a heat exchange section or recovery train 250. Heat exchange section 250 is designed to cool the produced synthesis gas stream 215 exiting the oxygen transport membrane reactor 210. In this illustrated embodiment, the heat exchange section 250 is also designed such that in cooling the synthesis gas stream 215, process steam 172 is generated, the combined hydrocarbon feed stream 133 is preheated, and boiler feed water 255 and feed water 259 are heated.

To minimize metal dusting issues, the hot synthesis gas product stream 215, preferably at a temperature between about 900° C. and 1050° C. is cooled to a temperature of about 400° C. or less in a Process Gas (PG) Boiler 252. The initially cooled synthesis gas product stream 254 is then used to preheat the mixture of natural gas and hydrogen feed stream 133 in a feed pre-heater 134 and subsequently to preheat boiler feed water 255 in the economizer 256 and to heat the feed water stream 259. In the illustrated embodiment, the boiler feed water stream 255 is preferably pumped using a feed water pump (not shown), heated in economizer 256 and sent to steam drum 257 while the heated feed water stream is sent to a de-aerator (not shown) that provides boiler feed water 255. Synthesis gas leaving the feed water heater 258 is preferably around 150° C. It is cooled down to about 40° C. using a fin-fan cooler 261 and a synthesis gas cooler 264 fed by cooling water 266. The cooled synthesis gas 270 then enters a knock-out drum 268 where water is removed from the bottoms as process condensate stream 271 which, although not shown, is recycled for use as feed water, and the cooled synthesis gas 272 is recovered overhead.

The final synthesis gas product 276 is obtained from the compression of the cooled synthesis gas stream 273 in a synthesis gas compressor 274. Depending on the application, multiple stages of compression may be required. The interstage cooling and condensate knock out is not shown in FIG. 1. Prior to such compression, however, a portion of the cooled synthesis gas stream 226 may optionally be recirculated to the reactor housing to form all or part of the low pressure hydrogen containing stream 222. Depending on the operating pressures of the oxygen transport membrane based reforming system, pressure of the recovered synthesis gas is preferably in the range of about 10 bar and 35 bar and more preferably in the range of 12 bar and 30 bar. The module of the final synthesis gas product produced in the described embodiment is typically about 1.8 to 2.3.

FIG. 2 is a schematic illustration of the oxygen transport membrane based reforming system of FIG. 1 tailored for and integrated with a methanol production process. In many regards, this embodiment is similar to the embodiment of FIG. 1 and, for sake of brevity, the description of the common aspects of the two embodiments will not be repeated here, rather, the following discussion shall focus on the differences. The syngas is typically compressed to between about 80 and 100 bar in syngas compressor 274. In the embodiment shown in FIG. 2, the final synthesis gas product 276 is mixed with a methanol loop recycle stream 310. This mixed stream 320 of compressed synthesis gas and methanol loop recycle is indirectly heated in heat exchanger 322 by the synthesized methanol stream 324 to a temperature between about 175° C. and 300° C. The heated stream 326 is directed to the methanol synthesis reactor 330. The exact heat arrangement will vary depending on the type of methanol synthesis reactor, technology vendor and approach to overall process integration, i.e. integrating with the front-end or syngas generation section. In this methanol synthesis reactor 330, hydrogen, carbon monoxide and carbon dioxide are consumed to produce methanol and water in an exothermic process through the following reactions:

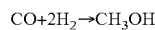

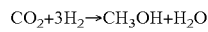

The heat generated in the methanol synthesis reaction is used for steam production and/or for preheating of the synthesis gas feed. Temperature at the outlet of the methanol reactor is typically between about 200° C. and about 260° C. This methanol synthesis stream 324 is cooled down to about 38° C. in heat exchanger 322 and cooler 332 before entering a separator 334 where the crude methanol stream 340 containing mostly methanol, water and trace amounts of other species (e.g. dimethyl ether, ethanol and higher alcohols), is separated in the bottoms and sent to further distillation steps for final purification. Most of the overhead stream 336 from the separator 334 is a methanol loop recycle stream 344 sent back to the methanol synthesis reactor 330 via recycle compressor 345 to increase the carbon conversion to methanol. The recycle compressor 345 is required to compensate for pressure drop across the methanol synthesis reactor 330 and associated equipment, e.g. heat exchangers and coolers.

A small portion of the overhead stream 336, typically between about 1% and 5% is purged from the methanol synthesis loop 300 to prevent buildup of inerts in the methanol synthesis loop 300. The typical composition of the purge stream 350 is as follows: 75% hydrogen, 3% carbon dioxide, 12% carbon dioxide, 3% nitrogen, and 7% methane, with a higher heating value of about 325 BTU/scf. The methanol loop purge stream 350 is then split into two streams, namely methanol purge stream 350A which is directed back to the auxiliary oxygen transport membrane reactor 220 as the hydrogen containing feed and methanol purge stream 350B which forms the hydrogen-rich gas that is combined with the hydrocarbon containing feed stream to form a combined hydrocarbon feed 133. In the illustrated embodiment, the low pressure hydrogen containing stream 222 is a mixture of a portion of the methanol purge stream 350A and a supplemental natural gas fuel stream 224.

Figure 3:
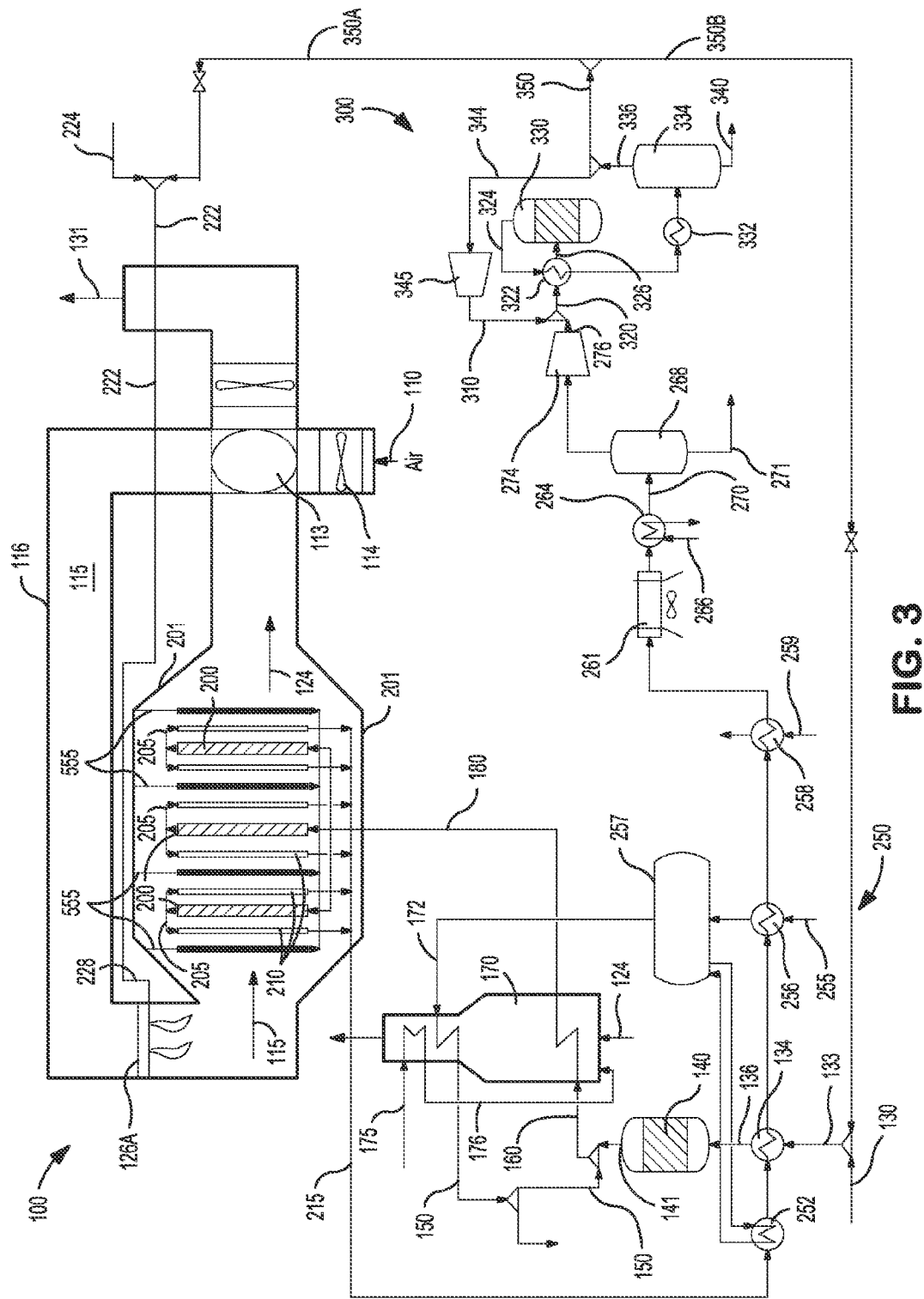
FIG. 3 is a schematic illustration of an alternate embodiment of an oxygen transport membrane based reforming system designed to carry out both a primary reforming process and a secondary reforming process within the oxygen transport membrane reactor using an auxiliary heat source comprising one or more ceramic burners.

FIG. 3 is a schematic illustration of an alternate embodiment of an oxygen transport membrane based reforming system designed to carry out both a primary reforming process and a secondary reforming process within the oxygen transport membrane reactor using an auxiliary heat source comprising one or more ceramic burners. In many regards, this embodiment is similar to the embodiment of FIG. 2 and, for sake of brevity, the description of the common aspects of the two embodiments will not be repeated here, rather, the following discussion shall focus only on the differences.

The main difference between the embodiment shown in FIG. 2 with the embodiment of FIG. 3 is that the third reactor consisting of a reactively driven oxygen transport membrane reactor is replaced with one or more porous ceramic burners (i.e. flameless burners) disposed in the reactor housing 201 proximate to the reforming reactor 200 and the reactively driven and catalyst containing oxygen transport membrane reactor 210. The one or more ceramic burners 555 are preferably configured to burn a light hydrocarbon containing stream using air or enriched air as the oxidant. When using a porous ceramic burner as the auxiliary heat source it is important to design the spatial arrangement of the ceramic burners vis-à-vis the oxygen transport membrane reactor and reforming reactor so as to maximize the thermal coupling and system efficiency while minimizing the mechanical complexity of the system. Unlike the use of oxygen transport membrane reactors, the use of porous ceramic burners within the reactor housing requires other design challenges and modifications of the system to fully integrate the burners as the auxiliary heat source. Such challenges and modifications may include providing a separate oxidant stream and/or a separate fuel source for the porous ceramic burners. In addition, the start-up procedures as well as the exhaust manifolding differences between the embodiments using the low pressure oxygen transport membrane reactor and those embodiments using one or more porous ceramic burners would be potentially significant and must taken into consideration.

Although not shown in FIG. 3 the porous ceramic or flameless burners may preferably be radiant tube type burners having a similar tubular or cylindrical configuration as the oxygen transport membrane reactor tubes depicted in FIGS. 1 and 2 with combustion occurring on the interior of the tube. Yet another ceramic burner configuration is to arrange a plurality of porous tubular ceramic burners with the fuel transport from the interior of the tube to the exterior surface with the combustion occurring on the outside surface using the oxygen depleted retentate stream as the oxidant. Still other contemplated arrangements of the auxiliary heat source may include a radial or circumferential ceramic burner arrangement or perhaps even a circumferential arrangement of the burner.

Another difference between the embodiments shown in FIG. 2 and FIG. 3 is that the duct burner 126A is disposed upstream of the reactor housing 201 in intake duct 116 and coupled to a supplemental fuel stream and/or the recirculated methanol purge stream 350B. In such arrangement, the operating conditions for the ceramic regenerator 113 are less severe and would save capital expense by allowing use of a smaller ceramic regenerator 113. If necessary, the duct burner 126A could instead be placed downstream of reactor housing 201 as in FIG. 2.

While the present invention has been characterized in various ways and described in relation to preferred embodiments, as will occur to those skilled in the art, numerous, additions, changes and modifications thereto can be made without departing from the spirit and scope of the present invention as set forth in the appended claims.

What is claimed is:

1. A method for producing a synthesis gas in an oxygen transport membrane based reforming system, the method comprising the steps of:
    reforming a hydrocarbon containing feed stream in a reforming reactor in the presence of a reforming catalyst disposed in the reforming reactor and heat to produce a reformed synthesis gas stream;
    feeding the reformed synthesis gas stream to a reactant side of a reactively driven and catalyst containing oxygen transport membrane reactor, wherein the oxygen transport membrane reactor includes at least one oxygen transport membrane element configured to separate oxygen from an oxygen containing stream at the oxidant side of the reactively driven and catalyst containing oxygen transport membrane reactor to the reactant side through oxygen ion transport when subjected to an elevated operational temperature and a difference in oxygen partial pressure across the at least one oxygen transport membrane element;
    reacting a portion of the reformed synthesis gas stream with oxygen permeated through the at least one oxygen transport membrane element to produce the difference in oxygen partial pressure across the at least one oxygen transport membrane element and generate reaction products and heat, including a first portion of the heat required for the reforming of the hydrocarbon containing feed stream supplied through the radiation mode of heat transfer; and
    reforming unreformed hydrocarbon gas in the reformed synthesis gas stream in the presence of one or more catalysts contained in the oxygen transport membrane reactor, the reaction products and the heat to produce a synthesis gas product stream;
    wherein a second portion of the heat required for the initial reforming step is transferred from an auxiliary heat source disposed proximate the reforming reactor through the radiation mode of heat transfer, wherein the auxiliary heat source provides between about 15% and 85% of the heat required for the initial reforming of the hydrocarbon containing feed stream in the reforming reactor.

2. The method of claim 1 wherein the heat generated as a result of the reaction of the reformed synthesis gas stream with permeated oxygen is transferred: (i) to the reformed synthesis gas stream present in the catalyst containing oxygen transport membrane reactor; (ii) to the reforming reactor; and (iii) to an oxygen depleted retentate stream.

3. The method of claim 1 wherein the auxiliary heat source is one or more reactively driven, oxygen transport membrane reactors.

4. The method of claim 3 wherein the reactively driven oxygen transport membrane reactor comprises a plurality of oxygen transport membrane elements disposed proximate the reforming reactor and configured to: (i) separate and transport oxygen from the oxygen containing stream contacting the oxidant side of the oxygen transport membrane element to the reactant side of the oxygen transport membrane element through oxygen ion transport; (ii) receive a hydrogen containing stream at the reactant side; and (iii) react the hydrogen containing stream with the permeated oxygen at the reactant side to produce the difference in oxygen partial pressure across the oxygen transport membrane element and to produce an auxiliary reaction product stream and heat.

5. The method of claim 4 wherein the hydrogen containing stream comprises a hydrogen and light hydrocarbon containing stream and the auxiliary reaction product stream exiting the reactant side is fed as a supplementary fuel to a duct burner or a fired heater or both.

6. The method of claim 4 wherein the one or more reactively driven oxygen transport membrane reactors are configured to receive a low pressure hydrogen containing stream at the reactant side, the pressure of the hydrogen containing stream being about 3 bar or less.

7. The method of claim 4 further comprising the step of feeding a portion of the synthesis gas product stream to the reactant side of the oxygen transport membrane elements to form all or part of the hydrogen containing stream.

8. The method of claim 4 wherein the produced synthesis gas is used in a methanol synthesis plant and the hydrogen containing stream further comprises a portion of a purge stream from the methanol synthesis plant.

9. The method of claim 1 wherein the hydrocarbon containing feed stream is a pre-reformed feed stream.

10. The method of claim 9 wherein the hydrocarbon containing feed stream is a pre-reformed in an adiabatic pre-reformer or a heated pre-reformer.

11. The method of claim 1 wherein the auxiliary heat source is one or more ceramic burners disposed proximate the reforming reactor and the reactively driven and catalyst containing oxygen transport membrane reactor, the one or more ceramic burners configured to burn a light hydrocarbon containing stream using air or enriched air as the oxidant.

* * * * *